(12) United States Patent
Kennedy et al.

(10) Patent No.: US 9,603,868 B1
(45) Date of Patent: Mar. 28, 2017

(54) POLYMER ADHESIVES COMPRISING A LOW BOILING POINT BIOCOMPATIBLE SOLVENT, HIGH MOLECULAR WEIGHT MULTI-ARM STAR CYANOACRYLATE-TELECHELIC POLYISOBUTYLENE AND 2-OCTYL CYANOACRYLATE

(71) Applicants: Joseph Kennedy, Akron, OH (US); Istvan Szanka, Balmazujvaros (HU); Amalia Szanka, Budapest (HU)

(72) Inventors: Joseph Kennedy, Akron, OH (US); Istvan Szanka, Balmazujvaros (HU); Amalia Szanka, Budapest (HU)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 14/940,626

(22) Filed: Nov. 13, 2015

(51) Int. Cl.
*A61K 31/785* (2006.01)
*A61K 31/275* (2006.01)
*A61L 24/06* (2006.01)

(52) U.S. Cl.
CPC .......... *A61K 31/785* (2013.01); *A61K 31/275* (2013.01)

(58) Field of Classification Search
CPC .. C10M 2205/0265; C10M 2217/0265; C10M 107/42; C10M 2217/026; C08L 23/20; C08L 101/02
See application file for complete search history.

(56) References Cited

U.S. PATENT DOCUMENTS

| | | |
|---|---|---|
| 7,341,716 B2 | 3/2008 | Porter |
| 2008/0243082 A1 | 10/2008 | Goodman |
| 2009/0264566 A1 | 10/2009 | Schambony et al. |
| 2014/0073743 A1* | 3/2014 | Kennedy .................. C08F 22/32 525/295 |

* cited by examiner

*Primary Examiner* — Anna Falkowitz
(74) *Attorney, Agent, or Firm* — Renner Kener Greive Bobak Taylor & Weber

(57) ABSTRACT

The present invention is directed to a substantially homogeneous miscible liquid adhesive composition comprising a relatively high number average molecular weight (Mn=6,000-10,000 g/mole) multi-arm star polymer having polyisobutylene chains terminated with cyanoacrylate groups (High-Ø(PIB-CA)$_3$); 2-octyl cyanoacrylate (Oct-CA); and a low boiling point biocompatible solvent having a boiling point of not more than 37° C. When this adhesive composition contacted with living tissue and reacted with a nucleophile, such as water or an initiator, the biocompatible solvent will evaporate and the High-Ø(PIB-CA)$_3$ and Oct-CA will co-polymerize in-situ to form a poly(2-octyl cyanoacrylate)-polyisobutylene co-network suitable for any of a number of biomedical applications, from wound closure and healing of skin tissue, to sealant for surgical cuts.

23 Claims, 3 Drawing Sheets

POLYMER ADHESIVES COMPRISING A LOW BOILING POINT BIOCOMPATIBLE SOLVENT, HIGH MOLECULAR WEIGHT MULTI-ARM STAR CYANOACRYLATE-TELECHELIC POLYISOBUTYLENE AND 2-OCTYL CYANOACRYLATE

FIELD OF THE INVENTION

In one or more embodiments, the present invention relates to polyisobutylene-based co-networks polymer co-network useful for wound closure and skin protection made without the use of toxic solvents. In particular, the invention relates to in-situ polymerizing surgical adhesives made from cyanoacrylate terminated multi-arm star polymer having polyisobutylene chains terminated with cyanoacrylate groups, 2-octyl cyanoacrylate, and a low boiling point biocompatible solvent.

BACKGROUND OF THE INVENTION

There is a great need in biomedical applications, including orthopedic practice, for sealants or adhesives of wounds and surgical cuts. Such sealants contemplated could range from sealants used for wound healing and wound closure on the skin to sealants used to permanently seal scalpel cuts and puncture wounds made by large bore injection needles in the course of various procedures.

At present, there is no satisfactory orthopedic sealant being used to satisfy the need for closing iatrogenic defects made in the annulus fibrosa during discectomies. This can cause serious problems in that the intervertebral disc may subsequently undergo accelerated degeneration, and the patient may require a spinal fusion some years later. Some implants have been proposed to resolve the issue but these were introduced without biomechanical considerations. Mechanical barriers have been recently proposed but are fundamentally different from an annulus sealant in that it (1) lacks the ability to reconstruct the annulus directly and restore motion, (2) cannot prevent the leakage of smaller particles from within the nucleus pulposus, (3) is more technically difficult to employ, and (4) would carry a significant risk of neurologic injury if extruded into the canal. No long term data is available on these products.

Further, there is also an unmet need for more flexible wound closure adhesives on the surface of the skin. Currently known wound closure adhesives include 2-octylcyanoacrylate (Oct-CA), known commercially by the brand name Dermabond®, available from Ethicon US LLC, a Johnson & Johnson company, wherein Dermabond® is a registered trademark of Johnson & Johnson Company, New Brunswick, N.J., and n-butyl-2-cyanoacrylate, known commercially by either Indermil® tissue adhesive, available from Covidien Co., a Henkel company, wherein Indermil® is a registered trademark of Henkel Corporation, Rocky Hill, Conn., or Histoacryl® topical skin adhesive, available from B. Braun Corporation, wherein Histoacryl® is a registered trademark of Aesculap, Inc., Center Valley, Pennsylvania. That is, it is well known that these monomers readily polymerize upon exposure to traces of moisture on surfaces such as skin. The CA group in these compounds is highly reactive toward nucleophiles because of the presence of the two highly electron withdrawing substituents (CN— and COO—), so that CA polymerizations are initiated by moisture. For instance, lower alkyl CAs such as methyl cyanoacrylates or ethyl cyanoacrylate (Superglue®) instantaneously polymerize in the presence of surface moisture. The rates of polymerizations are notably lower with the higher alkyl CAs (e.g., Oct-CA) due to the lower molar concentration of the CA groups.

Accordingly, attempts have been made to increase the rate of polymerization of these higher alkyl CAs (e.g., Oct-CA) without introducing any lower alkyl CAs, since the lower alkyl CAs are known to have toxicity concerns and cannot be used inside the body, but yet provide increase flexibility upon polymerization and higher viscosity than is normally available using commercially available wound closures containing 2-octyl-cyanoacrylate (Oct-CA) as the active ingredient. That is, commercial products such as Dermabond® are known to exhibit undesirably low viscosity (i.e., too runny) and to exhibit undesirable stiffness upon production (i.e., the coatings produced are too stiff and have low tensile strength).

More recently, and to overcome at least the stiffness problem, homopolymer networks containing cyanoacrylate-functionalized multi-arm polyisobutylene stars have been employed to provide more flexibility and rubberyness. These homopolymer networks have been developed and patented. The production of such polyisobutylenes provide for a core (Ø) with a desired number of polyisobutylene arms extending therefrom.

There are many potential biomedical applications with polyisobutylene with attachment of various polymers at the end of each arm. One clinical example where polyisobutylene has been adopted is poly(styrene-b-isobutylene-b-styrene), which is currently used as a coating in the Taxus® Drug Eluting Stent. Another potential application is for all applications where 2-octyl cyanoacrylate (Dermabond®) is currently employed and more flexibility is required.

To that end, cyanoacrylate-telechelic three-arm star polyisobutylenes have been prepared. Cyanoacrylate-telechelic three-arm star polyisobutylenes, Ø(PIB-CA)$_3$, were first prepared in 1991. A low viscosity syringible and injectable homopolymer functionalized with ethyl cyanoacrylate (i.e., Et-CA) was subsequently developed in 2007. It was found that a bolus of covalently linked PIB rubber "superglue" was created when Ø(PIB-CA)$_3$ was injected into (egg) protein and the properties could be controlled by addition of poly (ethyl-2-cyanoacrylate). On its own, Ø(PIB-CA)$_3$ has a tensile strength of 1.6 MPa, Young's Modulus of 4.9 MPa, and an elongation of 70%. Comparatively, the tensile strength of clinically available 2-octyl cyanoacrylate based "superglue", Dermabond® (Ethicon, J&J) and SurgiSeal™ (Adhezion Biomedical), is less than 0.1 MPa.

Furthermore, it was found that cyanoacrylate-ended tri-telechelic polyisobutylene Ø(PIB-CA)$_3$ (Mn~2500 g/mol or more) are nontoxic in rats in vivo. Without being bound by theory, it is believed that the biocompatible high barrier rubbery PIB moiety effectively envelops and shields the noxious cyanoacrylate groups from the surrounding tissue and the permanently sequestered -CA groups are rendered harmless. However, too high molecular weight Ø(PIB-CA)$_3$ could also render the benefit of the -CA groups useless as well, as the rate of polymerization would be greatly slowed.

As noted above, it took several years for the production of a co-network of Ø(PIB-CA)$_3$ and Et-CA. This is because Et-CA is not miscible with Ø(PIB-CA)$_3$. It was only by way of mechanical means (i.e., a dual injectable syringe) that the two components could be brought into contact with each other at a particular site for use. Moreover, the amount and molecular weight of Et-CA was such that only small amounts could be used. That is, the molar ratio of the Ø(PIB-CA)$_3$ to Et-CA was so high that the resultant product is today considered a homonetwork, rather than a co-network of Ø(PIB-CA)$_3$ and Et-CA. Thus, other alternative networks to Ø(PIB-CA)$_3$ and Et-CA were sought.

Even more recently, new co-networks consisting of relatively low molecular weight Ø(PIB-CA)$_3$ (Mn=1,000-4,000 g/mole) and Oct-CA have been developed. These low molecular weight Ø(PIB-CA)$_3$ and Oct-CA are miscible liquids and when reacted with an initiator will form a co-network. It has been found, however, that these polymer co-networks lack the mechanical properties desirable in a number of biomedical applications. Polymer co-networks formed from higher molecular weight Ø(PIB-CA)$_3$ (Mn>6,000 g/mole) and Oct-CA, on the other hand, have been found to have excellent mechanical properties but, because High-Ø(PIB-CA)$_3$ and Oct-CA, are not fully miscible, a solvent for both High-Ø(PIB-CA)$_3$ and Oct-CA, such as tetrahydrofuran (THF), must be used to permit miscibility. These solvents, however, are generally toxic and cannot be used in many medical and biological applications.

Accordingly, the need exists in the art for other co-networks formed by polymerizing multi-arm cyanoacrylate-functionalized polyisobutylene (Ø(PIB-CA)$_3$) and 2-octyl cyanoacrylate (Oct-CA) that have the desired mechanical characteristics, yet do not contain, or otherwise require for use, toxic solvents.

SUMMARY OF THE INVENTION

In general outline, the present invention is directed to a substantially homogeneous miscible liquid adhesive composition comprising a relatively high number average molecular weight (Mn=6,000-10,000 g/mole) multi-arm star polymer having polyisobutylene chains terminated with cyanoacrylate groups (High-Ø(PIB-CA)$_3$); 2-octyl cyanoacrylate (Oct-CA); and a low boiling point biocompatible solvent having a boiling point of not more than 37° C. When this adhesive composition contacted with living tissue and reacted with a nucleophile, such as water or an initiator, the biocompatible solvent will evaporate and the High-Ø(PIB-CA)$_3$ and Oct-CA will co-polymerize in-situ to form a poly(2-octyl cyanoacrylate)-polyisobutylene co-network suitable for any of a number of biomedical applications, from wound closure and healing of skin tissue, to sealant for surgical cuts.

In a first aspect, the present invention is directed to a liquid adhesive composition useful for wound closure and skin protection comprising: multiarm star polymer comprising polyisobutylene chains terminated with cyanoacrylate groups and having a number average molecular weight of from about 6,000 g/mole to about 10,000 g/mole; 2-octyl cyanoacrylate; and a low boiling point biocompatible solvent having a boiling point of not more than 37° C.; wherein both the multi-arm star polymer and the 2-octyl cyanoacrylate are miscible in the low boiling point biocompatible solvent. In some of these embodiments, the three- or four-arm star polymer has a number average molecular weight of about 6,500 g/mole. In one or more embodiments, the liquid adhesive composition of the present invention includes any one or more of the above referenced embodiments of the first aspect of the present invention wherein, the multi-arm star polymer is a three- or four-arm star polymer comprising polyisobutylene chains terminated with cyanoacrylate groups. In one or more embodiments, the liquid adhesive composition of the present invention includes any one or more of the above referenced embodiments of the first aspect of the present invention wherein the multi-arm star polymer is a cyanoacrylate tri-telechelic star polymer.

In one or more embodiments, the liquid adhesive composition of the present invention includes any one or more of the above referenced embodiments of the first aspect of the present invention wherein the low boiling point biocompatible solvent is a mixture of a $C_1$ to $C_3$ ether and a $C_3$ to $C_5$ alkane. In one or more embodiments, the liquid adhesive composition of the present invention includes any one or more of the above referenced embodiments of the first aspect of the present invention wherein the low boiling point biocompatible solvent mixture is selected from two groups; the first group consisting of diethyl ether, dimethyl ether, ethyl methyl ether, dibutyl ether, and combinations thereof and the second group consisting of propane, butane, isobutane, pentane, iso-pentane, and combinations thereof.

In one or more embodiments, the liquid adhesive composition of the present invention includes any one or more of the above referenced embodiments of the first aspect of the present invention wherein the weight ratio of the 2-octyl cyanoacrylate to the cyanoacrylate terminated three- or four-arm star polymer is from about 5:1 to about 40:1. In one or more embodiments, the liquid adhesive composition of the present invention includes any one or more of the above referenced embodiments of the first aspect of the present invention wherein the ratio of the 2-octyl cyanoacrylate to the three- or four-arm star polymer is from about 3:1 by weight to about 9:1 by weight.

In one or more embodiments, the liquid adhesive composition of the present invention includes any one or more of the above referenced embodiments of the first aspect of the present invention wherein the 2-octyl cyanoacrylate comprises from about 20% to about 60% of the composition by weight. In one or more embodiments, the liquid adhesive composition of the present invention includes any one or more of the above referenced embodiments of the first aspect of the present invention wherein the three- or four-arm star polymer comprises from about 15% to about 45% of the composition by weight. In one or more embodiments, the liquid adhesive composition of the present invention includes any one or more of the above referenced embodiments of the first aspect of the present invention wherein the low boiling point biocompatible solvent comprises from about 20% to about 40% of the composition by weight.

In a second aspect, the present invention is directed to a related method of forming a homogeneous polymer co-network useful for wound closure and skin protection using the liquid adhesive compositions described above comprising: first preparing a miscible composition having a multi-arm star polymer with polyisobutylene chains terminated with cyanoacrylate groups and having a number average molecular weight of from about 6,000 g/mole to about 10,000 g/mole; 2-octyl cyanoacrylate; and a low boiling point biocompatible solvent having a boiling point of not more than 37° C., wherein both the cyanoacrylate terminated multi-arm star polymer and the 2-octyl cyanoacrylate are miscible in the low boiling point biocompatible solvent; and second, applying the miscible composition to a tissue surface having one or more available nucleophiles, wherein the nucleophiles cause the composition to co-polymerize to form a homogeneous polymer co-network comprising the residues of the cyanoacrylate terminated multi-arm star polymer and the 2-octyl cyanoacrylate. In some of these embodiments, the cyanoacrylate telechelic multi-arm polymer has a number average molecular weight of about 6,500 g/mole.

In one or more embodiments, the method of the present invention includes any one or more of the above referenced embodiments of the second aspect of the present invention wherein said multi-arm star polymer with polyisobutylene chains terminated with cyanoacrylate groups is a cyanoacrylate terminated three- or four-arm star polymer. In one or more embodiments, the method of the present invention includes any one or more of the above referenced embodiments of the second aspect of the present invention wherein said multi-arm star polymer with polyisobutylene chains terminated with cyanoacrylate groups is a cyanoacrylate tri-telechelic star polymer.

In one or more embodiments, the method of the present invention includes any one or more of the above referenced embodiments of the second aspect of the present invention wherein the low boiling point biocompatible solvent is a mixture of a $C_1$ to $C_3$ ether and a $C_3$ to $C_5$ alkane. In one or more embodiments, the method of the present invention includes any one or more of the above referenced embodiments of the second aspect of the present invention wherein the low boiling point biocompatible solvent mixture is selected from two groups, the first group consisting of diethyl ether, dimethyl ether, ethyl methyl ether, dibutyl ether, and combinations thereof and the second group consisting of propane, butane, iso-butane, pentane, iso-pentane, and combinations thereof.

In one or more embodiments, the method of the present invention includes any one or more of the above referenced embodiments of the second aspect of the present invention wherein the weight ratio of the 2-octyl cyanoacrylate to the multi-arm star polymer in the composition is from about 5:1 to about 40:1. In one or more embodiments, the method of the present invention includes any one or more of the above referenced embodiments of the second aspect of the present invention wherein the ratio of the 2-octyl cyanoacrylate to the multi-arm star polymer in the composition is from about 3:1 to about 9:1 by weight.

In one or more embodiments, the method of the present invention includes any one or more of the above referenced embodiments of the second aspect of the present invention wherein the 2-octyl cyanoacrylate comprises from about 20% by weight to about 60% by weight of the miscible composition. In one or more embodiments, the method of the present invention includes any one or more of the above referenced embodiments of the second aspect of the present invention wherein the cyanoacrylate terminated multi arm star polymer comprises from about 15% by weight to about 45% by weight of the miscible composition. In one or more embodiments, the method of the present invention includes any one or more of the above referenced embodiments of the second aspect of the present invention wherein the low boiling point biocompatible solvent comprises from about 20% by weight to about 40% by weight of the miscible composition.

In one or more embodiments, the method of the present invention includes any one or more of the above referenced embodiments of the second aspect of the present invention wherein the step of applying the miscible composition further comprises applying an initiator to the miscible composition to initiate the co-polymerization.

BRIEF DESCRIPTION OF THE DRAWINGS

For a more complete understanding of the features and advantages of the present invention, reference is now made to the detailed description of the invention along with the accompanying figures in which.

DETAILED DESCRIPTION OF THE ILLUSTRATIVE EMBODIMENTS

In general outline, the present invention is directed to a substantially homogeneous miscible liquid adhesive composition comprising a relatively high number average molecular weight (Mn=6,000-10,000 g/mole) three- or four-arm star polymer having polyisobutylene chains terminated with cyanoacrylate groups (High-Ø(PIB-CA)$_3$); 2-octyl cyanoacrylate (Oct-CA); and a low boiling point biocompatible solvent having a boiling point of not more than 37° C. When this adhesive composition contacted with living tissue and reacted with a nucleophile, such as water or an initiator, the biocompatible solvent will evaporate and the High-Ø(PIB-CA)$_3$ and Oct-CA will co-polymerize in-situ to form a poly(2-octyl cyanoacrylate)-polyisobutylene co-network suitable for any of a number of biomedical applications, from wound closure and healing of skin tissue, to sealant for surgical cuts.

In a first aspect, the present invention is directed to a substantially homogeneous miscible liquid adhesive composition useful for wound closure and skin protection comprising: a multi-arm star polymer having polyisobutylene terminated with cyanoacrylate groups and a relatively high average molecular weight of from about 6,000 g/mole to about 10,000 g/mole (High-Ø(PIB-CA)$_3$); 2-octyl cyanoacrylate (Oct-CA); and a low boiling point biocompatible solvent having a boiling point of not more than 37° C. In some embodiments, the multi-arm star polymer having polyisobutylene terminated with cyanoacrylate groups may be a cyanoacrylate terminated three- or four-arm star polymer. In some embodiments, the multi-arm star polymer having polyisobutylene terminated with cyanoacrylate groups may be a cyanoacrylate tri-telechelic star polymer.

To begin, it will be appreciated that the chemical formulas of the starting monomers according to one or more embodiments of the present invention are shown below as formulas (I) and (II), below.

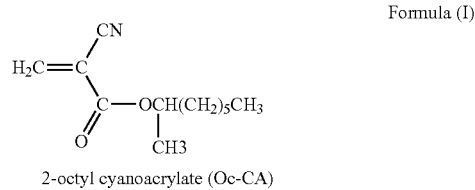

Formula (I)

2-octyl cyanoacrylate (Oc-CA)

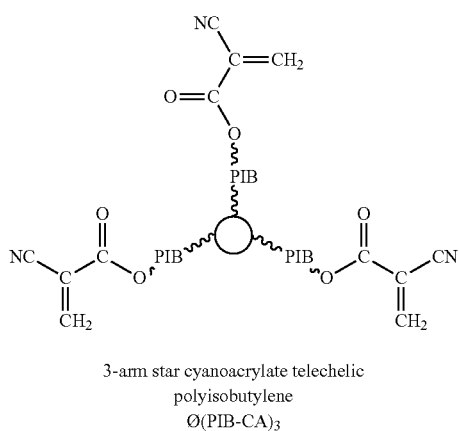

3-arm star cyanoacrylate telechelic
polyisobutylene
Ø(PIB-CA)$_3$

Figure 1A:
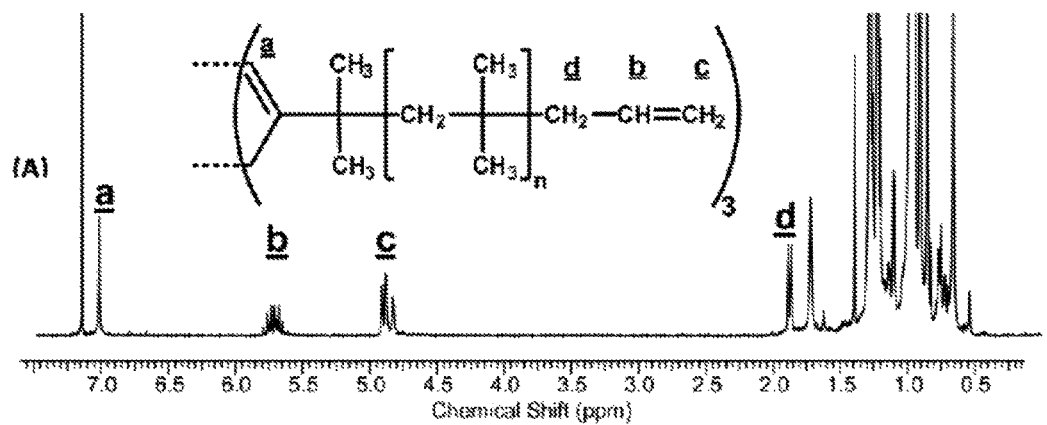
FIG. 1A is the H NMR spectrum of an allyl-telechelic three-arm star PIB intermediate.
Figure 1B:
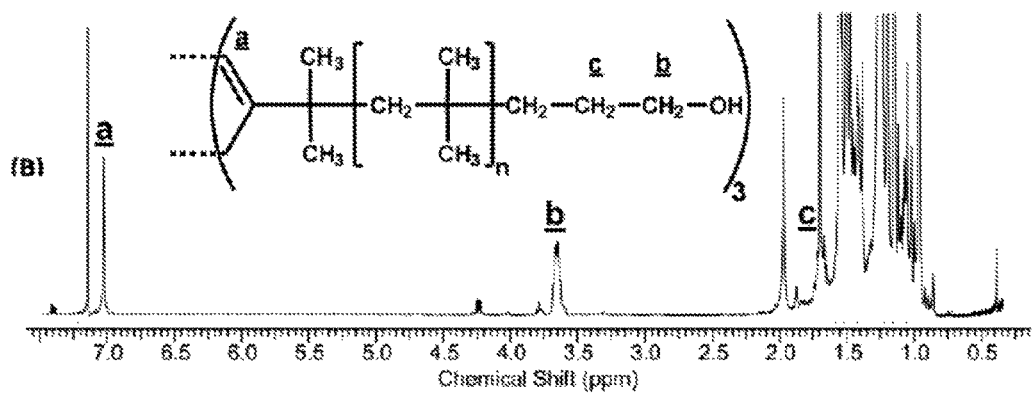
FIG. 1B is the H NMR spectrum of a hydroxyl-telechelic three arm star PIB intermediate.
Figure 1C:
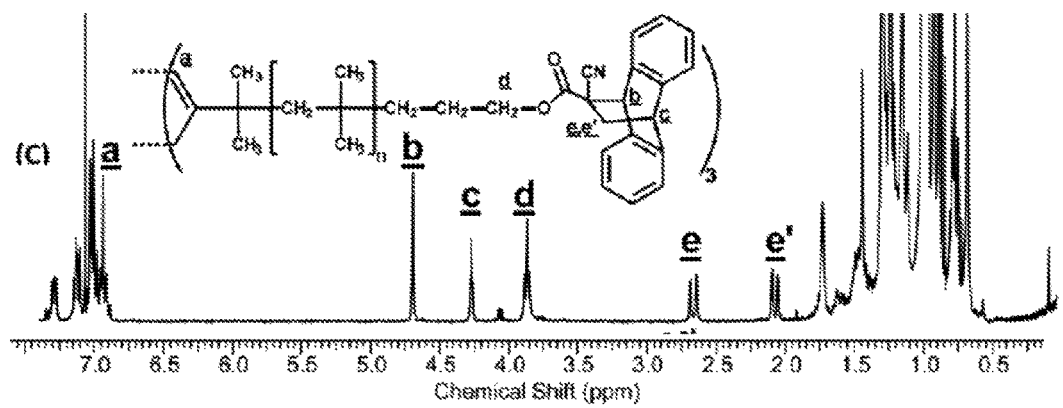
FIG. 1C is the H NMR spectrum of an anthracene/cyanoacrylate adduct telechelic three arm star PIB intermediate.
Figure 1D:
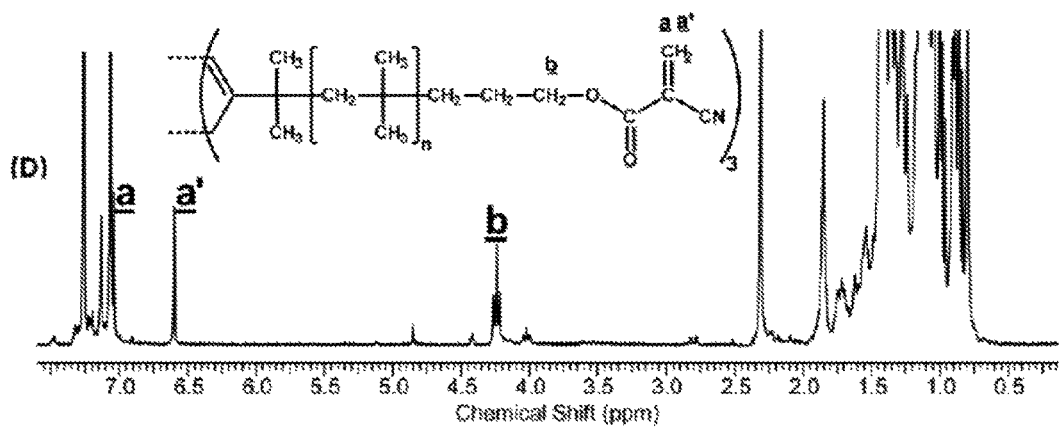
FIG. 1D is the H NMR spectrum the cyanoacrylate-tritelechelic PIB, Ø(PIB-CA)$_3$ final product.

As used herein, Ø(PIB-CA)$_3$ refers generally to a three- (or four-) arm star polymer having polyisobutylene chains terminated with cyanoacrylate groups, as shown in Formula II. The preparation of Ø(PIB-CA)$_3$ is well known and has been described in at least US Patent Application Publication No. US2014/0073743 A1, the disclosure of which is hereby incorporated by reference. Briefly, the synthesis involves the living polymerization of isobutylene induced by a trifunctional initiator and termination with allyltrimethylsilane. The 3-arm star allyl-terminated intermediate so obtained is converted quantitatively to the hydroxyl or bromine terminated intermediate, which is then reacted with anthracene-protected cyanoacryloyl chloride, or, preferentially, with 2-cyanoacrylic acid. Finally, the protective anthracene group was removed by treatment with maleic anhydride in refluxing xylene for about 10 hours to yield the target Ø(PIB-CA)$_3$. FIGS. 1A-C show the NMR spectra of the intermediates (allyl-, hydroxyl-, and anthracene/cyanoacrylate adduct) and FIG. 1D shows the NMR sprectra of the final product (cyanoacrylate-tri-telechelic PIBs, Ø(PIB-CA)$_3$).

Earlier syntheses of Ø(PIB-CA)$_3$ carried out by the use of (protected) cyanoacryloyl chloride consistently gave yellow products. Efforts to remove the color (repeated precipitations, column chromatography, treatment with activated carbon) were only partially successful. The source of the discoloration is unknown (most likely due to traces of impurities associated with the use of thionyl chloride). In contrast, esterification of Ø(PIB-OH)$_3$ with anthracene-protected 2-cyanoacrylic acid gave colorless products (10). The following equation (Scheme 1) outlines this preferred method for the synthesis of Ø(PIB-CA)$_3$ (The protective anthracene group, indicated by A in the semi-circle, can be readily removed by maleic anhydride):

Scheme 1

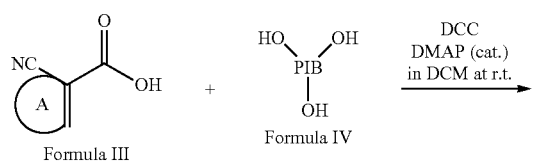

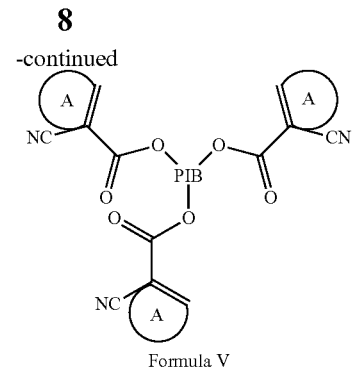

Formula V

Thus, in a 50 mL Schlenk flask with a magnetic stir bar were placed under a blanket of nitrogen Ø(PIB-OH)$_3$ (1.227 g, M$_n$=2500 g/mol) (Formula IV), anthracene-protected 2-cyano carboxylic acid adduct (1.333 g) (Formula III), and 4-dimethylamino pyridine (DMAP, 71.3 mg) dissolved in dichloromethane (DCM, 25 mL). Then the solution was cooled to 0° C., N,N'-dicyclohexylcarbodiimide (DCC, 1.0648 g) was added, the solution was stirred for 30 min at 0° C., and then overnight at room temperature. The precipitated urea was filtered off, the DCM was evaporated in vacuo, and the viscous residue was dissolved in THF and purified by two precipitations into methanol to produce an anthracene/cyanoacrylate adduct three arm star PIB intermediate (Formula V). Finally, to yield Ø(PIB-CA)$_3$, the protective anthracene group was removed by treatment with maleic anhydride in refluxing xylene for 8 hrs. According to NMR analysis the yields of protection and deprotection were typically ~60 and ~90%, respectively. Similar yields have been obtained by others who used the same protection/deprotection technique.

And while Ø(PIB-CA)$_3$ polymers having a wide range of number average molecular weights (M$_n$) are known in the art, the present application primarily relates to Ø(PIB-CA)$_3$ polymers having number average molecular weights (MO, the present application related to Ø(PIB-CA)$_3$ polymers having number average molecular weights (M$_n$) of from about 6,000 g/mole to about 10,000 g/mole. It is known that Ø(PIB-CA)$_3$ polymers having somewhat lower number average molecular weights (M$_n$) of from about 1,000 g/mole to about 4,000 g/mole are miscible with Oct-CA, which is surprising in light of the fact that very similar cyanoacrylates (i.e. methyl-, ethyl-, and butyl-CA) are completely immiscible with (Ø(PIB-CA)$_3$). Co-networks of these lower molecular weight Ø(PIB-CA)$_3$ polymers and Oct-CA, do not require a solvent to prepare, but also lack the mechanical properties desirable in a number of biomedical applications.

Polymer co-networks formed from higher molecular weight Ø(PIB-CA)$_3$ (Mn>6,000 g/mole) and Oct-CA, on the other hand, have been found to have excellent mechanical properties and are suitable for a wide variety of biomedical applications, from wound closure and healing of skin tissue, to sealant for surgical cuts. Specifically, a 25/75 High-Ø (PIB-CA)$_3$ (M$_n$=6500 g/mol)/Oct-CA co-network shows a yield point at ~10% strain, after which it exhibits impressive rubbery properties with ~6 MPa tensile strength and ~180% elongation. These properties are comfortably in excess of those required of a wound closure adhesive. While much larger Ø(PIB-CA)$_3$ polymers may be known in the art, as used herein, the terms "high" or "relatively high" as applied to Ø(PIB-CA)$_3$ polymers refers to multi-arm star polymers having polyisobutylene chains terminated with cyanoacrylate groups as shown shown in Formula II, that: (i) are not fully miscible with Oct-CA, and (ii) have a $M_n$ of from about 6,000 g/mole to about 10,000 g/mole (High-Ø(PIB-CA)$_3$).

In some embodiments, the High-Ø(PIB-CA)$_3$ in the liquid adhesive composition may have a $M_n$ of from about 6,000 g/mole to about 10,000 g/mole. In some other embodiments, the High-Ø(PIB-CA)$_3$ in the liquid adhesive composition may have a $M_n$ of from about 6,000 g/mole to about 9,000 g/mole. In some other embodiments, the High-Ø(PIB-CA)$_3$ in the liquid adhesive composition may have a $M_n$ of from about 6,000 g/mole to about 8,000 g/mole. In some other embodiments, the High-Ø(PIB-CA)$_3$ in the liquid adhesive composition may have a $M_n$ of from about 6,000 g/mole to about 7,000 g/mole. In some other embodiments, the High-Ø(PIB-CA)$_3$ in the liquid adhesive composition may have a $M_n$ of from about 6,000 g/mole to about 6,500 g/mole. In some other embodiments, the High-Ø(PIB-CA)$_3$ in the liquid adhesive composition may have a $M_n$ of from about 6,500 g/mole to about 9,000 g/mole. In some other embodiments, the High-Ø(PIB-CA)$_3$ in the liquid adhesive composition may have a $M_n$ of from about 6,500 g/mole to about 8,000 g/mole. In some other embodiments, the High-Ø(PIB-CA)$_3$ in the liquid adhesive composition may have a $M_n$ of about 6,500 g/mole.

In some embodiments, the High-Ø(PIB-CA)$_3$ comprises from about 15% by weight to about 45% by weight of the liquid adhesive compositions of the present invention. In some embodiments, the High-Ø(PIB-CA)$_3$ comprises from about 15% by weight to about 35% by weight of the liquid adhesive compositions of the present invention. In some embodiments, the High-Ø(PIB-CA)$_3$ comprises from about 15% by weight to about 30% by weight of the liquid adhesive compositions of the present invention. In some embodiments, the High-Ø(PIB-CA)$_3$ comprises from about 15% by weight to about 25% by weight of the liquid adhesive compositions of the present invention. In some embodiments, the High-Ø(PIB-CA)$_3$ comprises from about 25% by weight to about 40% by weight of the liquid adhesive compositions of the present invention. In some embodiments, the High-Ø(PIB-CA)$_3$ comprises from about 30% by weight to about 40% by weight of the liquid adhesive compositions of the present invention. In some embodiments, the High-Ø(PIB-CA)$_3$ comprises from about 20% by weight to about 30% by weight of the liquid adhesive compositions of the present invention. In some embodiments, the High-Ø(PIB-CA)$_3$ comprises about 23.5% by weight of the liquid adhesive compositions of the present invention. In some embodiments, the High-Ø(PIB-CA)$_3$ comprises about 25% by weight of the liquid adhesive compositions of the present invention.

The preparation of Oct-CA is likewise well known in the art and will not be decribed herein in detail. Oct-CA is commercially available from a variety of sources, including, but not limited to, Chenso Inc. (Champions Gate, Fla.). In some embodiments, the 2-octyl cyanoacrylate (Oct-CA) may comprise from about 20% by weight to about 60% by weight of the liquid adhesive composition. In some other embodiments, the Oct-CA may comprise from about 20% by weight to about 50% by weight of the liquid adhesive composition. In some other embodiments, the Oct-CA may comprise from about 20% by weight to about 40% by weight of the liquid adhesive composition. In some other embodiments, the Oct-CA may comprise from about 20% by weight to about 30% by weight of the liquid adhesive composition. In some other embodiments, the Oct-CA may comprise from about 30% by weight to about 60% by weight of the liquid adhesive composition. In some other embodiments, the Oct-CA may comprise from about 40% by weight to about 60% by weight of the liquid composition. In some other embodiments, the Oct-CA may comprise from about 50% by weight to about 60% by weight of the liquid composition. In some other embodiments, the Oct-CA may comprise from about 30% by weight to about 50% by weight of the liquid composition.

In some embodiments, the weight ratio of Oct-CA to High-Ø(PIB-CA)$_3$ in the liquid adhesive compositions of the present invention may be from about 5:1 to about 40:1. In some embodiments, the weight ratio of Oct-CA to High-Ø(PIB-CA)$_3$ in the liquid adhesive compositions of the present invention may be from about 10:1 to about 40:1. In some embodiments, the weight ratio of Oct-CA to High-Ø(PIB-CA)$_3$ in the liquid adhesive compositions of the present invention may be from about 20:1 to about 40:1. In some embodiments, the weight ratio of Oct-CA to High-Ø(PIB-CA)$_3$ in the liquid adhesive compositions of the present invention may be from about 30:1 to about 40:1. In some embodiments, the weight ratio of Oct-CA to High-Ø(PIB-CA)$_3$ in the liquid adhesive compositions of the present invention may be from about 5:1 to about 30:1. In some embodiments, the weight ratio of Oct-CA to High-Ø(PIB-CA)$_3$ in the liquid adhesive compositions of the present invention may be from about 5:1 to about 20:1. In some embodiments, the weight ratio of Oct-CA to High-Ø(PIB-CA)$_3$ in the liquid adhesive compositions of the present invention may be from about 5:1 to about 10:1. In some embodiments, the weight ratio of Oct-CA to High-Ø(PIB-CA)$_3$ in the liquid adhesive compositions of the present invention may be from about 10:1 to about 30:1. In some embodiments, the weight ratio of Oct-CA to High-Ø(PIB-CA)$_3$ in the liquid adhesive compositions of the present invention may be from about 15:1 to about 25:1.

In some embodiments, the ratio of Oct-CA to High-Ø(PIB-CA)$_3$ in the liquid adhesive compositions of the present invention may be from about 3:1 by weight to about 9:1 by weight. In some embodiments, the ratio of Oct-CA to High-Ø(PIB-CA)$_3$ in the liquid adhesive compositions of the present invention may be from about 5:1 by weight to about 9:1 by weight. In some embodiments, the ratio of Oct-CA to High-Ø(PIB-CA)$_3$ in the liquid adhesive compositions of the present invention may be from about 7:1 by weight to about 9:1 by weight. In some embodiments, the ratio of Oct-CA to High-Ø(PIB-CA)$_3$ in the liquid adhesive compositions of the present invention may be from about 3:1 by weight to about 8:1 by weight. In some embodiments, the ratio of Oct-CA to High-Ø(PIB-CA)$_3$ in the liquid adhesive compositions of the present invention may be from about 3:1 by weight to about 6:1 by weight. In some embodiments, the ratio of Oct-CA to High-Ø(PIB-CA)$_3$ in the liquid adhesive compositions of the present invention may be from about 3:1 by weight to about 4:1 by weight. In some embodiments, the ratio of Oct-CA to High-Ø(PIB-CA)$_3$ in the liquid adhesive compositions of the present invention may be from about 4:1 by weight to about 8:1 by weight. In some embodiments, the ratio of Oct-CA to High-Ø(PIB-CA)$_3$ in the liquid adhesive compositions of the present invention may be from about 5:1 by weight to about 7:1 by weight.

Because High-Ø(PIB-CA)$_3$ and Oct-CA are not fully miscible and room temperature, prior art systems used a solvent for both High-Ø(PIB-CA)$_3$ and Oct-CA, such as tetrahydrofuran (THF), must be used to permit miscibility. These solvents, however, are generally toxic and cannot be used in many medical and biological applications. To avoid the problems associated with the use of toxic solvents like THF, the liquid adhesive compositions of various embodiments of the present invention utilize a low boiling point biocompatible solvent, such as diethyl ether, having a boiling point at or below the body temperature of the patient to render High-Ø(PIB-CA)$_3$ and Oct-CA fully miscible. As used herein, the term "biocompatible" refers to a material that can come into contact with a living system without producing an adverse effect. Diethyl ether, for example, is known to be biocompatible, having been used as an anesthetic inhalant in the 20$^{th}$ Century, and has a boiling point of 36.5° C., which is below the ordinary human body temperature of 37° C. In some embodiments, the low boiling point biocompatible solvent is a $C_1$ to $C_3$ ether. In some embodiments, the low boiling point biocompatible solvent mixture is selected from two groups, the first group consisting of diethyl ether, dimethyl ether, ethyl methyl ether, dibutyl ether, and combinations thereof and the second group consisting of propane, butane, iso-butane, pentane, iso-pentane, and combinations thereof.

In some embodiments, the low boiling point biocompatible solvent may comprise from about 20% by weight to about 40% by weight of the liquid adhesive composition. In some embodiments, the low boiling point biocompatible solvent may comprise from about 25% by weight to about 40% by weight of the liquid adhesive composition. In some embodiments, the low boiling point biocompatible solvent may comprise from about 30% by weight to about 40% by weight of the liquid adhesive composition. In some embodiments, the low boiling point biocompatible solvent may comprise from about 35% by weight to about 40% by weight of the liquid adhesive composition. In some embodiments, the low boiling point biocompatible solvent may comprise from about 20% by weight to about 35% by weight of the liquid adhesive composition. In some embodiments, the low boiling point biocompatible solvent may comprise from about 20% by weight to about 30% by weight of the liquid adhesive composition. In some embodiments, the low boiling point biocompatible solvent may comprise from about 20% by weight to about 25% by weight of the liquid adhesive composition. In some embodiments, the low boiling point biocompatible solvent may comprise from about 25% by weight to about 35% by weight of the liquid adhesive composition.

The order of mixing of the Oct-CA, the High-Ø(PIB-CA)$_3$, and the low boiling point biocompatible solvent is not particularly limited, as any mixing sequence gives a homogeneous system.

The low boiling point biocompatible solvents of the liquid adhesive compositions of the present invention has several significant advantages over THF and similar solvents known and used in the art for this purpose. To begin with, these solvents are, unlike THF, non-toxic and can, therefore, be used as an adhesive for tissues within the body. Moreover, the low boiling point biocompatible solvents used in the present invention will begin to evaporate upon contact with the patient's skin and will continue to evaporate as the poly(Oct-CA-co-High-Ø(PIB-CA)$_3$) network forms. Although it varies, most warm blooded mammals have a normal body temperature of from about 36° C. to about 40° C., with humans having a normal body temperature of about 37° C. Accordingly, since all of the low boiling point biocompatible solvents used in the present invention have boiling points at or below these temperatures, substantially all of the solvent will dissolve as it reaches the body temperature of the patient. In addition, during the solvent evaporation the temperature of the skin decreases causing an analgesic effect.

In another aspect, the present invention is directed to a method of making the substantially homogeneous miscible liquid adhesive compositions described above. In some embodiments, the method comprises: (1) preparing any of the substantially homogeneous miscible liquid adhesive composition a miscible compositions described above; and (2) applying the miscible composition to a tissue surface having one or more available nucleophiles, wherein the nucleophiles cause the composition to co-polymerize to form a homogeneous polymer co-network comprising the residues of the cyanoacrylate terminated multi-arm star polymer (e.g., High-Ø(PIB-CA)$_3$) and the 2-octyl cyanoacrylate (Oct-CA). In some embodiments, the homogeneous polymer co-network may comprise the residues of a cyanoacrylate terminated three- or four-arm star polymer. In some embodiments, the homogeneous polymer co-network may comprise the residues of a cyanoacrylate tri-telechelic star polymer. As used herein, the term "residue(s)" is used to refer generally to the part of a monomer or other chemical unit that has been incorporated into a polymer or large molecule. Here, by extension, the residues of High-Ø(PIB-CA)$_3$ and Oct-CA molecules are the portions of the those molecules that are incorporated into homogeneous polymer co-networks of the present invention.

Because it is a liquid, the liquid adhesive compositions of the present invention can be delivered by essentially any means known in the art to form a coating or film that preferably rapidly solidifies into a robust rubbery protecting barrier. In one embodiment, the liquid adhesive composition may be delivered by spraying or application via vial with plastic sponge tip to provide a suitable coating or film of the composition onto the desired tissue. In another embodiment, the liquids may be delivered by syringe, injecting the composition to a suitable site, again using the sponge tip. It should be appreciated that, in these embodiments, this sponge performs two critical functions: (a) it helps delivering the active ingredient evenly over the targeted surface, and, more importantly, (b) it contains a key component, the initiator, which induces and accelerates the polymerization of the CA monomer as it is squeezed through the sponge. By allowing such monomer mixtures to polymerize in situ, solid rubbery plugs can form exactly where the mixture was applied, i.e., where the seal is needed.

As set forth above, the copolymerization of Oct-CA with High Ø(PIB-CA)$_3$ may be initiated by the moisture (i.e., nucleophilic groups such as OH, NH$_2$, etc.) on or within the skin, blood or other living (or dead) tissue itself when one of the liquid adhesive compositions of the present invention described above is sprayed, coated or otherwise applied over wounds or surgical cuts. However, it has been found that the rate of co-polymerization can be significantly increased by the use of a suitable initiator, applied just before application of the liquid adhesive composition to the skin, wound, or surgical cut. The scientific literature mentions a large variety of initiators for the polymerization of alkyl CAs, e.g., water, bases, anions, methanol, amines, phosphines, and alkyl ammonium salts. One of ordinary skill in the art will be able to select a suitable initiator without undue experimentation. Suitable initiators may include, without limitation N,N-dimethyl-p-toluidine (DMT), (commercially available from, at least, Sigma Aldrich Company LLC (St. Louis, Mo.)), azabicyclo[2.2.2]-octane (ABCO), and 1,4-diazabicyclo[2.2.2]-octane (DABCO), (both ABCO and DABCO are commercially available from, at least, Alfa Aesar (Ward Hill, Mass.)).

During the early stages of polymerization the viscosity of the system is relatively low and propagation, i.e., the attack of the first CA anion to Oct-CA and/or Ø(PIB-CA)₃ (that yields crosslinking) is relatively unhindered as set forth in Scheme 2 below:

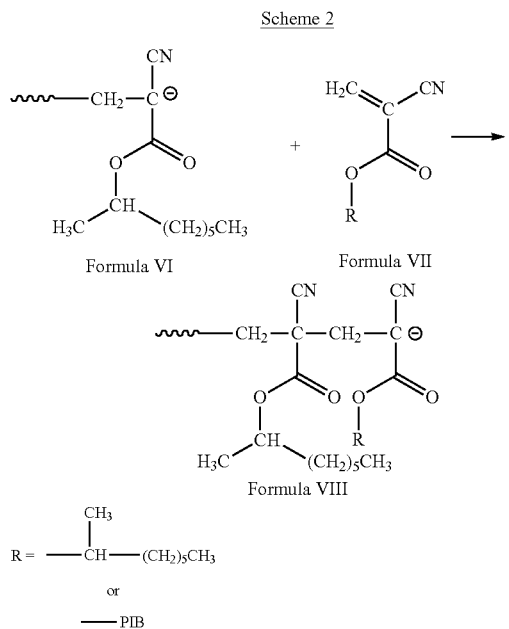

Upon further propagation steps, particularly after Ø(PIB-CA)₃ incorporation, the viscosity of the system rises very rapidly and the rate of (co)polymerization necessarily drops precipitously. Ultimately, a fraction of CA groups likely become entrapped in the highly viscous matrix and propagation ceases.

Due to the highly hydrophobic matrix, termination, i.e., the permanent annihilation of propagating anions, which likely involves reaction with protons (i.e., moisture), is absent or is very slow in these bulk polymerizations. The mechanical properties of the products may be controlled by controlling the relative proportions of the rubbery PIB and glassy poly(Oct-CA) segments. By increasing the length of the PIB arms, elongations increase and moduli decrease. The longer poly(Oct-CA) sequences would phase separate and may function as reinforcing sites.

Further, because High-Ø(PIB-CA)₃ and Oct-CA both contain polymerizable cyanoacrylate (CA) groups and the inherent reactivity of the CA functional group is independent of the molecular weight of the polymer it is attached to, it may be safely assumed that the reactivities of the CA groups of Oct-CA and High -Ø(PIB-CA)₃ molecules are essentially identical (i.e., their reactivity ratios are unity). The composition of the co-network will, therefore, reflect the relative composition of the starting monomers and the co-network composition can therefore, be controlled by controlling the relative amounts of High-Ø(PIB-CA)₃, Low-Ø(PIB-CA)₃ and Oct-CA.

Figure 2:
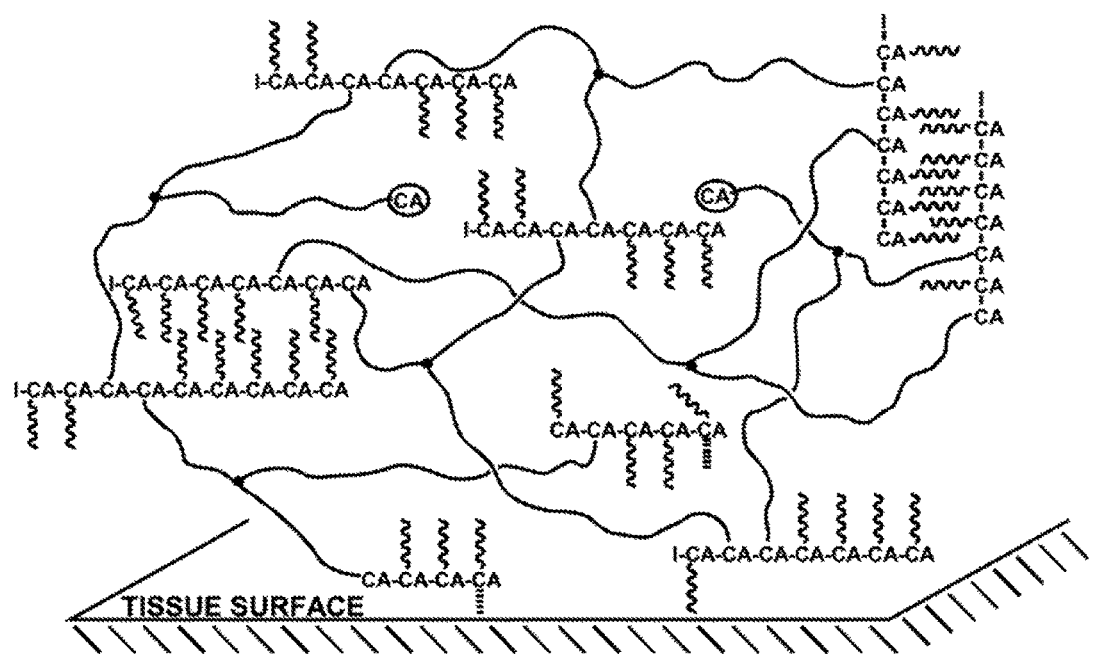
FIG. 2 is an idealized microstructure representation of a polyisobutylene co-network that arises from a homogeneous 50/50 wt/wt polymer blend of Oct-CA plus Ø(PIB-CA)$_3$ upon the addition of an initiator at room temperature, wherein the poly(Oct-CA) sequences polymerized are of sufficient length (i.e., greater than 3 CA units) to form separate coalesced phases whose $T_g$ can be identified by appropriate instrumentation such as Differential Scanning calorimetry (DSC) or Dynamic Mechanical Thermal Analysis (DMTA).

FIG. 2 shows an idealized microstructure of a co-network that arises in situ from a liquid adhesive compositions according to one or more embodiment of the present invention comprising a 50/50 wt/wt blend of Oct-CA and Ø(PIB-CA)₃, upon the addition of a nucleophile or suitable initiator at room temperature. In these co-networks, the poly(Oct-CA) sequences are of sufficient length (i.e., greater than 3 CA units) to form separate coalesced phases whose $T_g$ can be identified by appropriate instrumentation. FIG. 2 shows aspects of the resulting 50/50 wt/wt Poly[Oc-CA-co-Ø(PIB-CA)₃] co-network, with the wiggly lines being PIB, "I" being the initiator, and "CA---" being the Oct-CA bonded to or available for bonding to the skin surface, the CA of multiple units being the Poly(Oct-CA), the CAs in the circle being "useless" CA groups entrapped in matrix, and the "•" being the aromatic center of Ø(PIB-CA)₃. Again the presence of catenated/entrapped crosslinks and PIB loops should be noted. Importantly, the polymerization of CA groups is initiated by a purposely added initiator (I), in addition to a nucleophilic group (N or O) in the epidermis (---), or by traces of moisture (not shown). It should also be appreciated, however, that FIG. 2 is intended to show a generalized microstructure for a Oct-CA/Ø(PIB-CA)₃ co-network and its interaction with skin, and does not reflect the ratio of Oct-CA to High-Ø(PIB-CA)₃ described above.

In light of the foregoing, it should be appreciated that the present invention significantly advances the art by providing a liquid adhesive composition that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Materials 2-octyl cyanoacrylate (Oct-CA) was purchased from Chenso, and they were used without further purification. Tetrahydrofuran, purchased from Aldrich and toluene were thoroughly dried by refluxing and distilling the solvents over sodium and benzophenone.

Instruments and Procedures

Proton (¹H) NMR spectroscopy, (Varian Gemini 300 and 500 MHz instruments and deuterated chloroform as solvent) was used to determine chemical structures, chain-end functionalities and molecular weights ($M_n$).

Gel permeation chromatography (GPC) eluograms were obtained using a Waters GPC instrument equipped with a series of three Waters Styragel-HR columns (HR-1, HR-4E, HR-5E), a refractive index detector (Waters 2414) and a multiangle laser light scattering detector (Dawn EOS, Wyatt Technology). Samples were dissolved in THF, the flow rate was 1 mL THF/min, and column temperature was 35° C.

Example 1

Synthesis of Ø(PIB-CA)$_3$

In a 50 mL Schlenk flask with a magnetic stir bar were placed under a blanket of nitrogen Ø(PIB-OH)$_3$ (1.227 g, M$_n$=2500 g/mol), anthracene-protected 2-cyano carboxylic acid adduct (1.333 g), and 4-dimethylamino pyridine (DMAP, 71.3 mg) dissolved in dichloromethane (DCM, 25 mL). Then the solution was cooled to 0° C., N,N'-dicyclohexylcarbodiimide (DCC, 1.0648 g) was added, the solution was stirred for 30 min at 0° C., and then overnight at room temperature. The precipitated urea was filtered off, the DCM was evaporated in vacuo, and the viscous residue was dissolved in THF and purified by two precipitations into methanol. Finally, to yield Ø(PIB-CA)$_3$, the protective anthracene group was removed by treatment with maleic anhydride in refluxing xylene for 8 hrs. According to NMR analysis the yields of protection and deprotection were typically ~60 and ~90%, respectively. Similar yields have been obtained by others who used the same protection/deprotection technique.

Example 2

Solubility of Oct-CA and High- Ø(PIB-CA)$_3$ in Diethyl Ether

Homogeneous optically clear solutions were obtained when Oct-CA or Ø(PIB-CA)$_3$ of Mn −6,500 ng/mol was placed in diethyl ether at room temperature. Both Oct-CA and Ø(PIB-CA)$_3$ of Mn-6,500 g/mole were soluble in diethyl ether and formed homogeneous optically clear ether solutions at room temperature.

Example 3

Synthesis of Liquid Adhesive Composition

A mixture of 3.26 g (76.5 wt %) Oct-CA and 1.01 g (23.5 wt %) Ø(PIB-CA)$_3$ having a Mn of 6,500 g/mol was mixed in 0.8 mL diethyl ether to produce 4.8 mL of a mixture. This mixture produced a slightly hazy solution, which upon heating to 35° C. (close to the boiling point of diethyl ether) became optically clear. This homogeneous solution did not phase separate standing for 1 hr at room temperature. After storing the solution at room temperature for 72 hrs, two phases formed indicating phase separation.

What is claimed is:

1. A liquid adhesive composition useful for wound closure and skin protection comprising:
   a multi-arm star polymer comprising polyisobutylene chains terminated with cyanoacrylate groups and having a number average molecular weight of from about 6,000 g/mole to about 10,000 g/mole;
   2-octyl cyanoacrylate; and
   a low boiling point biocompatible solvent having a boiling point of not more than 37° C.;
   wherein both said multi-arm star polymer and said 2-octyl cyanoacrylate are miscible in said low boiling point biocompatible solvent.

2. The liquid adhesive composition of claim 1 wherein said multi-arm star polymer is a three- or four-arm star polymer comprising polyisobutylene chains terminated with cyanoacrylate groups.

3. The liquid adhesive composition of claim 1 wherein said multi-arm star polymer is a cyanoacrylate tri-telechelic star polymer.

4. The liquid adhesive composition of claim 1 wherein said multi-arm star polymer has a number average molecular weight of about 6,500 g/mole.

5. The liquid adhesive composition of claim 1 wherein said low boiling point biocompatible solvent is a $C_1$ to $C_3$ ether.

6. The liquid adhesive composition of claim 1 wherein said low boiling point biocompatible solvent is selected from the group consisting of diethyl ether, dimethyl ether, ethyl methyl ether, dibutyl ether, and combinations thereof.

7. The liquid adhesive composition mixture of claim 1 wherein the weight ratio of said 2-octyl cyanoacrylate to said multi-arm star polymer is from about 5:1 to about 40:1.

8. The liquid adhesive composition mixture of claim 1 wherein the ratio of said 2-octyl cyanoacrylate to said cyanoacrylate terminated multi-arm star polymer is from about 3:1 by weight to about 9:1 by weight.

9. The liquid adhesive composition mixture of claim 1 wherein said 2-octyl cyanoacrylate comprises from about 20% to about 60% of said liquid adhesive composition by weight.

10. The liquid adhesive composition of claim 1 wherein said cyanoacrylate terminated multi-arm star polymer comprises from about 15% to about 45% of said liquid adhesive composition by weight.

11. The liquid adhesive composition of claim 1 wherein said low boiling point biocompatible solvent comprises from about 20% to about 40% of said liquid adhesive composition by weight.

12. A method of forming a homogeneous polymer co-network useful for wound closure and skin protection using the liquid adhesive composition of claim 1 comprising:
   A. preparing a miscible liquid adhesive composition comprising:
      a multi-arm star polymer comprising polyisobutylene terminated with cyanoacrylate groups and having a number average molecular weight of from about 6,000 g/mole to about 10,000 g/mole;
      2-octyl cyanoacrylate; and
      a low boiling point biocompatible solvent having a boiling point of not more than 37° C.
      wherein both said cyanoacrylate terminated multi-arm star polymer and said 2-octyl cyanoacrylate are miscible in said low boiling point biocompatible solvent; and
   B. applying said miscible liquid adhesive composition to a tissue surface having one or more available nucleophiles, wherein said nucleophiles cause said composition to co-polymerize to form a homogeneous polymer co-network comprising the residues of said cyanoacrylate terminated multi-arm star polymer and said 2-octyl cyanoacrylate.

13. The method of claim 12 wherein said multi-arm star polymer is a three- or four-arm star polymer comprising polyisobutylene chains terminated with cyanoacrylate groups.

14. The method of claim 12 wherein said multi-arm star polymer is a cyanoacrylate tri-telechelic star polymer.

15. The method of claim 12 wherein said multi-arm star polymer has a number average molecular weight of about 6,500 g/mole.

16. The method of claim 12 wherein said low boiling point biocompatible solvent is a $C_1$ to $C_3$ ether or $C_3$ to $C_5$ alkane.

17. The method of claim 12 wherein said low boiling point biocompatible solvent mixture is selected a first group or a second group, wherein said first group consists of diethyl ether, dimethyl ether, ethyl methyl ether, dibutyl ether, and combinations thereof and said second group consists of propane, butane, iso-butane, pentane, iso-pentane, and combinations thereof.

18. The method of claim 12 wherein the weight ratio of said 2-octyl cyanoacrylate to said cyanoacrylate terminated multi-arm star polymer in said miscible liquid adhesive composition is from about 5:1 to about 40:1.

19. The method of claim 12 wherein the ratio of said 2-octyl cyanoacrylate to said cyanoacrylate terminated multi-arm star polymer in said miscible liquid adhesive composition is from about 3:1 to about 9:1 by weight.

20. The method of claim 12 wherein said 2-octyl cyanoacrylate comprises from about 20% by weight to about 60% by weight of said miscible liquid adhesive composition.

21. The method of claim 12 wherein said cyanoacrylate terminated multi-arm star polymer comprises from about 15% by weight to about 45% by weight of said miscible liquid adhesive composition.

22. The method of claim 12 wherein said low boiling point biocompatible solvent comprises from about 20% by weight to about 40% by weight of said miscible liquid adhesive composition.

23. The method of claim 12 wherein the step of applying said miscible liquid adhesive composition further comprises applying an initiator to said miscible liquid adhesive composition to initiate the co-polymerization.

\* \* \* \* \*